(12) United States Patent
Yin

(10) Patent No.: US 9,131,698 B2
(45) Date of Patent: Sep. 15, 2015

(54) BIOCIDAL COMPOSITIONS AND METHODS OF USE

(75) Inventor: Bei Yin, Buffalo Grove, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/125,095

(22) PCT Filed: May 8, 2012

(86) PCT No.: PCT/US2012/036882
§ 371 (c)(1),
(2), (4) Date: Mar. 7, 2014

(87) PCT Pub. No.: WO2012/173715
PCT Pub. Date: Dec. 20, 2012

(65) Prior Publication Data
US 2014/0221318 A1    Aug. 7, 2014

Related U.S. Application Data

(60) Provisional application No. 61/496,069, filed on Jun. 13, 2011.

(51) Int. Cl.
*A01N 25/34* (2006.01)
*A01N 25/00* (2006.01)
*A01N 57/00* (2006.01)
*A61K 31/66* (2006.01)
*A01N 47/10* (2006.01)
*A61K 31/27* (2006.01)
*A01N 33/00* (2006.01)
*A01N 57/20* (2006.01)
*A01N 47/44* (2006.01)

(52) U.S. Cl.
CPC ............ *A01N 57/20* (2013.01); *A01N 47/44* (2013.01)

(58) Field of Classification Search
None
See application file for complete search history.

(56) References Cited

U.S. PATENT DOCUMENTS

| | | | |
|---|---|---|---|
| 7,491,334 B2 * | 2/2009 | Comstock | 210/652 |
| 2006/0065598 A1 * | 3/2006 | Comstock | 210/639 |
| 2007/0048356 A1 | 3/2007 | Schorr et al. | |
| 2008/0142453 A1 | 6/2008 | Unhoch et al. | |
| 2010/0286096 A1 | 11/2010 | Yin et al. | |
| 2010/0297719 A1 * | 11/2010 | de Sa et al. | 435/161 |
| 2012/0178722 A1 | 7/2012 | Yin | |

FOREIGN PATENT DOCUMENTS

| | | | | |
|---|---|---|---|---|
| JP | 11071208 A | | 3/1999 | |
| WO | WO 2007/018946 | * | 2/2007 | B01D 61/02 |
| WO | WO 2009/001205 | * | 12/2008 | C12N 1/16 |

* cited by examiner

*Primary Examiner* — Jeffrey T Palenik
(74) *Attorney, Agent, or Firm* — Tifani M. Edwards

(57) ABSTRACT

Provided are biocidal compositions comprising: a hydroxymethyl-substituted phosphorus compound and a polymeric biguanide. The compositions are useful for controlling microorganisms in aqueous or water-containing systems.

6 Claims, No Drawings

BIOCIDAL COMPOSITIONS AND METHODS OF USE

CROSS-REFERENCE TO RELATED APPLICATION

This application claims priority from provisional application Ser. No. 61/496,069, filed Jun. 13, 2011, which is incorporated herein by reference in its entirety.

FIELD OF THE INVENTION

The invention relates to biocidal compositions and methods of their use for the control of microorganisms in aqueous and water-containing systems. The compositions comprise a hydroxymethyl-substituted phosphorus compound and a polymeric biguanide.

BACKGROUND OF THE INVENTION

Protecting water-containing systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Biofilm, formed by microorganism growth, can create even greater problem and potentially causes huge economic losses in industry through equipment and pipeline corrosion, system plugging, product failing, and energy losses. Biofilm is formed by a buildup of layers of microorganisms occupying a structured community encapsulated within a self developed polymeric matrix. Microorganisms within the biofilm are known as sessile microorganisms, whereas free floating non-biofilm microorganisms are planktonic.

By growing in biofilms, sessile microorganisms are more tolerant to antimicrobial treatment and biocides that are effective against planktonic microorganisms may not exhibit equivalent efficacy against sessile bacteria inside a biofilm. Moreover, even biocides that are effective against biofilm-associated microorganisms are not necessarily efficient at removing a biofilm from a contaminated surface. The physical presence of the remnants of the biofilm (e.g., exopolysaccharides and dead bacteria cells) still plug systems and oil/gas reservoirs, and lead to an uneven availability of oxygen to e.g., a metal surface that allows corrosion to occur. Thus, killing microorganisms in a biofilm without removing the biofilm from a surface may not always solve the contamination problem.

There exists a continuing need for biocides that are effective against a wide range of microorganisms, that may be used in reduced amounts so as to be economically and environmentally attractive, and that exhibit the ability to remove biofilm.

BRIEF SUMMARY OF THE INVENTION

In one aspect, the invention provides biocidal compositions. The compositions are useful for controlling microbial growth in aqueous or water-containing systems, including for applications in the oil and natural gas industry. The compositions of the invention comprise: a hydroxymethyl-substituted phosphorus compound selected from the group consisting of a tetrakis(hydroxymethyl)phosphonium salt, a $C_1$-$C_3$ alkyl- or $C_2$-$C_3$ alkenyl-tris(hydroxymethyl)phosphonium salt, and tris(hydroxymethyl)phosphine; and a polymeric biguanide.

In a second aspect, the invention provides a method for controlling microorganisms in aqueous or water-containing systems. The method comprises treating the system with an effective amount of a biocidal composition as described herein.

DETAILED DESCRIPTION OF THE INVENTION

As noted above, the invention provides biocidal compositions and methods of using them in the control of microorganisms. The compositions comprise a hydroxymethyl-substituted phosphorus compound and a polymeric biguanide. It has surprisingly been discovered that combinations of a hydroxymethyl-substituted phosphorus compound and a polymeric biguanide as described herein, at certain weight ratios, are synergistic when used for microorganism control in aqueous or water-containing media. That is, the combined materials result in improved biocidal properties than would otherwise be expected based on their individual performance at the particular use-concentration. The observed synergy permits reduced amounts of the materials to be used to achieve acceptable biocidal properties.

In addition to exhibiting synergy, the compositions of the invention are effective at controlling both aerobic and anaerobic microorganisms. Further, the compositions exhibit the ability to remove biofilm. As a result of these attributes, the compositions are well suited for use in various applications, including in the oil and natural gas industry where biocidal agents are needed that are capable of controlling microorganisms, including aerobic and anaerobic microorganisms, and that are effective against biofilm.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism growth.

The composition of the invention comprises: a hydroxymethyl-substituted phosphorus compound and a polymeric biguanide.

The hydroxymethyl-substituted phosphorus compound for use in the invention is selected from the group consisting of a tetrakis(hydroxymethyl)phosphonium salt, a $C_1$-$C_3$ alkyl- or $C_2$-$C_3$ alkenyl-tris(hydroxymethyl)phosphonium salt, and tris(hydroxymethyl)phosphin. Such compounds are generally available both in undissolved form or as aqueous solutions. In one embodiment of the invention, the hydroxymethyl-substituted phosphorus compound is a tetrakis(hydroxymethyl)phosphonium salt, such as the chloride, phosphate, or sulfate salt. A preferred compound is tetrakis(hydroxymethyl) phosphonium sulfate (THPS). THPS is available from The Dow Chemical Company as AQUCAR™ THPS 75, a 75 wt % solution in water. Of course, more than one of the recited hydroxymethyl-substituted phosphorus compounds can be combined for use in the present invention; in such cases, ratios and concentrations are calculated using the total weight of all hydroxymethyl-substituted phosphorus compounds.

In some embodiments of the invention, the polymeric biguanide compound is polyhexamethylene biguanide. The material may be the free base or it may be in the form of a salt. Suitable salts include, but are not limited to, the chloride salt.

Polymeric biguanides are commercially available or they may be readily prepared by those skilled in the art.

In some embodiments, the weight ratio of the hydroxymethyl-substituted phosphorus compound to the polymeric biguanide in the compositions of the invention is between 30:1 and 1:30, or alternatively between 17:1 and 1:17, or alternatively between 17:1 and 1:1 alternatively between 1:1 and 1:17, or alternatively between 1:1 and 1:2.

In some embodiments, the weight ratio is between 17:1 and 1:17, alternatively between 17:1 and 1:1, alternatively between 3.5:1 and 1:1, and the aqueous or water containing system treated with the composition comprises anaerobic microorganisms. In some embodiments, the system is contacted with the biocide for at least 2 hours.

In some embodiments, the weight ratio is between 17:1 and 1:17, or alternatively between 1:1 and 1:2, and the aqueous or water containing system treated with the composition comprises aerobic microorganisms. In some embodiments, the system is contacted with the biocide for at least 24 hours.

The compositions of the invention are useful for controlling microorganisms in aqueous or water-containing systems. In some embodiments, the aqueous or water containing system comprises at least 40 weight percent, alternatively at least 60 weight percent, or alternatively at least 80 weight percent of water. Non-limiting examples of aqueous or water containing systems with which the inventive compositions may be used to control microorganisms include those present in oil and natural gas applications. Examples of such systems include, but are not limited to, injection and produced water, source water for waterflooding and hydraulic fracturing such as pond water and holding tank water, functional fluids such as drilling muds, completion or workover fluids, hydrotest fluids, stimulation fluids, packer fluids, and fracturing fluids, oil and gas wells, separation, storage, and transportation systems, oil and gas pipelines, oil and gas vessels, or fuel.

The inventive compositions may also be used for controlling microorganisms in other industrial aqueous and water containing/contaminated systems, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care and household products such as detergent, membrane and filtration systems, toilet bowl, textiles, leather and leather production system, or a system used therewith.

In some embodiments, the microorganism being controlled with the compositions of the invention is anaerobic, such as SRB. In some embodiments, the microorganism being controlled is anaerobic, such as SRB, and the aqueous system contains a reducing agent, such as sulfide.

A person of ordinary skill in the art can readily determine, without undue experimentation, the concentration of the composition that should be used in any particular application. By way of illustration, a suitable actives concentration (total for both the hydroxymethyl-substituted phosphorus compound and the polymeric biguanide) is typically between 1 and 2500 ppm, alternatively between 5 and 1000 ppm, alternatively between 10 and 500 ppm, or alternatively between 50 and 300 ppm, based on the total weight of the aqueous or water-containing system including the biocides. In some embodiments for oil and gas applications, it is preferred that active concentrations of the composition range from about 10 to about 300 ppm by weight, preferably about 30 to 100 ppm, for top side treatment, and from about 30 to about 500 ppm, preferably about 50 to about 250 ppm, for downhole treatment.

The components of the inventive compositions can be added to the aqueous or water-containing system separately, or preblended prior to addition. A person of ordinary skill in the art can easily determine the appropriate method of addition. The composition can be used in the system with other additives such as, but not limited to, surfactants, ionic/non-ionic polymers and scale and corrosion inhibitors, oxygen scavengers, and/or additional biocides.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

The following examples are illustrative of the invention but are not intended to limit its scope. Unless otherwise indicated, ratios, percentages, parts, and the like used herein are by weight.

EXAMPLES

The synergy indexes reported in the following examples are calculated using the following equation:

$$\text{Synergy Index} = Ca/CA + Cb/CB$$

Ca: Concentration of biocide A required to achieve a certain level of bacterial kill when used in combination with B CA: Concentration of biocide A required to achieve a certain level of bacterial kill when used alone Cb: Concentration of biocide B required to achieve a certain level of bacterial kill when used in combination with A CB: Concentration of biocide B required to achieve a certain level of bacterial kill when used alone.

A synergy index (SI) of 1 indicates additivity, a synergy index of less than 1 indicates synergy, and a synergy index greater than 1 indicates antagonism.

Example 1

Synergistic Effect of Tetrakis (Hydroxymethyl) Phosphonium Sulfate (THPS) and Polyhexamethylene Biguanide (PHMB), Against Anaerobic Bacteria in 24 Hours Inside an anaerobic chamber (Bactron anaerobic chamber), a deoxygenated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na2SO_4$, 43.92 mg of $Na_2CO_3$ in 1 L water) is inoculated with *Desulfovibrio longus* ATCC 51456 to a final bacterial concentration of $10^6$ to $10^7$ CFU/mL. Aliquots of this cell suspension are then treated with THPS, PHMB, and THPS/PHMB blends, at selected active concentrations. After the treated cell suspensions are incubated at 35° C. for 24 hours, the biocidal efficacy is determined by minimum tested biocide concentration for 99.999% bacterial reduction in the aliquots. Table 1 summarizes the efficacy of each biocide and their blends, and provides Synergy Index of each combination.

TABLE 1

Biocidal efficacy and Synergy Index (against anaerobic bacteria)

| Active weight ratio of THPS:PHMB | Concentration (ppm a.i.) for anaerobic bacteria kill | | Synergy Index |
|---|---|---|---|
| | THPS | PHMB | |
| 1:0 | 8.8 | 0.0 | |
| 16.9:1 | 5.9 | 0.3 | 0.80 |
| 7.6:1 | 5.9 | 0.8 | 0.96 |

TABLE 1-continued

Biocidal efficacy and Synergy Index (against anaerobic bacteria)

| Active weight ratio of | Concentration (ppm a.i.) for anaerobic bacteria kill | | Synergy |
|---|---|---|---|
| THPS:PHMB | THPS | PHMB | Index |
| 3.4:1 | 3.9 | 1.2 | 0.89 |
| 1:1 | 1.7 | 1.7 | 0.87 |
| 1:3.4 | 0.8 | 2.6 | 1.09 |
| 0:1 | 0.0 | 2.6 | | a.i. = active ingredient

As shown in Table 1, THPS in combination with PHMB exhibits a synergistic effect against anaerobic bacteria.

Example 2

Synergistic Effect of THPS and PHMB Against Anaerobic Bacteria in 2 Hours

The same test method as described in Example 1 is performed to test the biocidal efficacy of THPS, PHMB, and the combinations of these two biocides in 2 hour treatment time. Table 2 summarizes the efficacy of each biocide and combination, and the Synergy Index of each combination.

TABLE 2

Biocidal efficacy of THPS, PHMB, and their combinations against SRB in 2 hours and Synergy Index

| Active weight ratio of | Concentration (ppm a.i.) for complete SRB kill | | Synergy |
|---|---|---|---|
| THPS:PHMB | THPS | PHMB | Index |
| 1:0 | 22.2 | 0.0 | |
| 1:2.3 | 4.4 | 9.9 | 0.86 |
| 1:5.1 | 2.0 | 9.9 | 0.76 |
| 1:7.6 | 1.3 | 9.9 | 0.73 |
| 1:11.5 | 0.9 | 9.9 | 0.71 |
| 1:17.2 | 0.6 | 9.9 | 0.69 |
| 0:1 | 0.0 | 14.8 | |

As shown by the data in Table 1 and Table 2, the combination of THPS and PHMB is synergistic against anaerobic bacteria at an active weight ratio range of from 17:1 to 1:17 (16.9:1 to 1:17.2).

Example 3

Synergistic Effect of THPS and PHMB Against Aerobic Bacteria in 2 Hours

A sterile salt solution (0.2203 g of CaCl$_2$, 0.1847 g of MgSO$_4$, and 0.2033 g of NaHCO$_3$ in 1 L water) is inoculated with approximately $10^7$ CFU/mL of *Pseudomonas aeruginosa* ATCC 10145 and *Staphylococcus aureus* ATCC 6538. Aliquots of the cell suspension are then treated with THPS, PHMB, and combinations of these actives at selected concentrations. After incubating at 37° C. for 2 hr, the biocidal efficacy is determined by minimum biocide concentration for complete bacterial kill in the aliquots. Synergy Index is then calculated. Table 3 summarizes the efficacy of each biocide and their combinations, and the Synergy Index of each combination.

TABLE 3

Biocidal efficacy and Synergy Index (against aerobic bacteria)

| Active weight ratio of | Concentration (ppm a.i.) for aerobic bacteria kill | | Synergy |
|---|---|---|---|
| THPS:PHMB | THPS | PHMB | Index |
| 1:0 | 50 | 0 | |
| 4:1 | 50 | 6 | 1.50 |
| 2:1 | 25 | 6 | 1.00 |
| 1:1 | 13 | 6 | 0.75 |
| 1:2 | 6 | 6 | 0.63 |
| 1:4 | 6 | 13 | 1.13 |
| 1:8 | 3 | 13 | 1.06 |
| 0:1 | 0 | 13 | |

Example 4

Biocidal Effect of THPS and PHMB Against Aerobic Bacteria in 24 Hours

A sterile 0.85% NaCl saline water solution is inoculated with *Pseudomonas aeruginosa* ATCC 10145 and *Staphylococcus aureus* ATCC 6538 at final bacterial concentration of about $10^7$ cells per mL. Aliquots of the cell suspension are then treated with THPS, PHMB, and their combinations at selected concentrations. After incubating at 37° C. for 24 hours, viable bacteria in the aliquots are enumerated using a serial dilution method. The biocidal efficacy is determined by minimum biocide concentration for 99.9% bacterial kill in the aliquots. Synergy Index is then calculated. Table 4 summarizes the efficacy of each biocide and their combinations, and the Synergy Index of each combination.

TABLE 4

Biocidal efficacy against aerobic bacteria in 24 hours and Synergy Index

| Active weight ratio of | Concentration (ppm a.i.) for 99.9% bacterial kill | | Synergy |
|---|---|---|---|
| THPS:PHMB | THPS | PHMB | Index |
| 1:0 | 19.8 | 0.0 | |
| 17.1:1 | 8.8 | 0.5 | 0.58 |
| 11.4:1 | 13.2 | 1.2 | 0.96 |
| 7.6:1 | 19.8 | 2.6 | 1.67 |
| 3.4:1 | 13.2 | 3.9 | 1.67 |
| 1:1 | 2.6 | 2.6 | 0.80 |
| 1:3.4 | 0.8 | 2.6 | 0.71 |
| 1:7.6 | 0.3 | 2.6 | 0.68 |
| 1:11.4 | 0.2 | 2.6 | 0.68 |
| 1:17.1 | 0.2 | 2.6 | 0.67 |
| 0:1 | 0.0 | 3.9 | |

As show by Table 4, the combination of THPS and PHMB is synergistic against aerobic bacteria at an active weight ratio range of from 17:1 to 1:17 (17.1:1 to 1:17.1).

Example 5

Biofilm Removal with THPS/PHMB Combination

Biofilms of *Desulfovibrio longus* ATCC 51456 are grown in a Calgary Biofilm Device (Innovotech, Alberta, Canada) at 35° C. and under anaerobic conditions for 72 hours with shaking (125 rpm). Modified Baar's Medium (ATCC #1249 Broth) is used as culture medium and the medium is changed after 48 hrs of incubation. After the incubation period, pegs are rinsed with deoxygenated 0.85% NaCl solution and then treated with THPS and THPS/PHMB blend (2.3:1 active weight ratio) in a deoxygenated salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3, 20 mg of Fe(NH4) 2 (SO4) 2.6H2O in 1 L water) for 2 hours. After biocide treatment, the pegs are rinsed again with deoxygenated sterile 0.85% NaCl solution and then the total biofilm left on each peg is measured according to the following description. The biofilm is fixed with 99% methanol and, after air drying, the pegs are stained with 2% (w/v) crystal violet and washed with tap water. The pegs are then air dried and the crystal violet bound to the biofilm is extracted with 33% glacial acetic acid. The total remaining biofilm is determined by the optical density (OD) of the extracted solution at 580 nm. Table 5 compares the remaining biofilm after biocide treatment for the tested biocides.

TABLE 5

Remaining biofilm (optical density of biofilm captured crystal violet) after treatment with THPS-PHMB combination and THPS

| Biocide | ppm active | $OD_{580}$ |
|---|---|---|
| THPS | 200 | 1.03 |
|  | 50 | 0.59 |
| THPS:PHMB at 2.3:1 active weight | 200 | 0.19 |
|  | 50 | 0.34 |

Table 5 shows that THPS-PHMB combination has great biofilm removing capability compared to THPS used alone.

What is claimed is:

1. A synergistic composition effective for controlling anaerobic bacteria comprising: a tetrakis (hydroxymethyl) phosphonium sulfate and polyhexamethylene biguanide or a salt thereof
   wherein the weight ratio the tetrakis (hydroxymethyl) phosphonium sulfate and polyhexamethylene biguanide is between 17:1 and 1:1.

2. A method for controlling microorganisms in an aqueous or water-containing system, the method comprising treating the system with the composition of claim 1.

3. The method of claim 2 wherein the aqueous or water-containing system is used or is present in oil or gas production.

4. The method of claim 3 wherein oil or gas production comprises injection and produced water, source water for waterflooding and hydraulic fracturing, pond water, holding tank water, functional fluids, drilling muds, completion and workover fluids, hydrotest fluids, stimulation fluids, packer fluids, fracturing fluids, oil and gas wells, separation, storage and transportation systems, oil and gas pipelines, oil and gas vessels, or fuel.

5. The method of claim 2 wherein the aqueous or water-containing system is cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care and household products such as detergent, membrane and filtration systems, toilet bowel, textiles, leather and leather production system, or a system used therewith.

6. The method of claim 2 wherein the microorganisms are anaerobic bacteria.

* * * * *